United States Patent [19]

Castaldi et al.

[11] Patent Number: 4,764,642
[45] Date of Patent: Aug. 16, 1988

[54] PROCESS FOR PREPARING OPTICALLY ACTIVE ALPHA-HALOALKYL-ARYL-KETONES

[75] Inventors: Graziano Castaldi, Briona; Silvia Cavicchioli, Costermano; Claudio Giordano, Vicenza, all of Italy

[73] Assignee: Zambon S.p.A., Vicenza, Italy

[21] Appl. No.: 915,573

[22] Filed: Oct. 6, 1986

[30] Foreign Application Priority Data

Oct. 4, 1985 [IT] Italy ................. 22356 A/85

[51] Int. Cl.⁴ .............................................. C07C 45/59
[52] U.S. Cl. .................... 568/319; 568/322; 568/43
[58] Field of Search .................. 549/450, 45, 452; 568/319, 322, 43

[56] References Cited

FOREIGN PATENT DOCUMENTS 0087807  9/1983  European Pat. Off. ............ 549/450
0158255 10/1985  European Pat. Off. ............ 549/450
0158913 10/1985  European Pat. Off. ............ 549/450

Primary Examiner—James H. Reamer
Attorney, Agent, or Firm—Cushman, Darby & Cushman

[57] ABSTRACT

A process is described for preparing alpha-haloalkyl-aryl-ketones, comprising reacting a substantially anhydrous strong acid with a ketal of formula

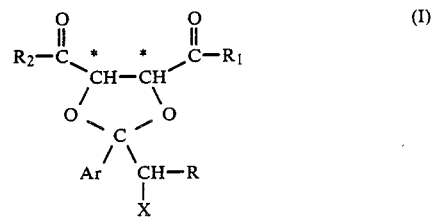

in which Ar, R, $R_1$, $R_2$ and X have the meanings given in the description.

5 Claims, No Drawings

PROCESS FOR PREPARING OPTICALLY ACTIVE ALPHA-HALOALKYL-ARYL-KETONES

This invention relates to a process for preparing optically active alpha-haloalkyl-aryl-ketones.

Alpha-haloalkyl-aryl-ketones are useful intermediates in the synthesis of organic compounds, for example compounds of pharmaceutical activity or compounds useful in agriculture.

In certain cases the availability of optically active alpha-haloalkyl-aryl-ketones is very useful. A typical example of this requirement is the synthesis of optically active alpha-aryl-alkanoic acids which are used in pharmaceutics.

These acids can be prepared from optically active alpha-haloalkyl-aryl-ketones by forming ketals with glycols or alcohols and rearranging them. The main known rearrangement methods are reported in Angew. Chem. Int. Ed. 23, 413 (1984) and in the description of European patent application No. 81993 (Syntex).

This latter publication describes a process for preparing optically active alpha-haloethyl-aryl-ketones by a coupling or Friedel-Crafts reaction between an aromatic compound and the optically active alpha-bromo-propionyl-bromide. This latter, which is prepared from lactic acid and alanine, racemises at temperatures exceeding $-10°$ C. [J. Am. Chem. Soc. 76, 6054 (1954)], making implementation of the process of an industrial scale difficult.

Italian patent application Nos. 7204 A/84, 7206 A/84 and 7207 A/84 in the name of the present applicant describe ketals obtained from alkyl-aryl-ketones and L(+) or D(−)-tartaric acid or derivatives, their diastereoselective halogenation and their use in the preparation of optically active alpha-arylalkanoic acids. The ketal intermediates described in the said italian patent applications have the following formula

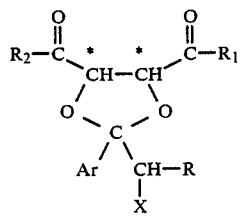

in which
Ar represents an aryl, possibly substituted;
R represents a $C_1$-$C_4$ alkyl;
$R_1$ and $R_2$, which can be the same or different, represent a hydroxyl, an alkoxy, an amino group possibly mono- or di-substituted, or a $O^-M^+$ group where $M^+$ represents the cation of an alkaline metal;
X represents, inter alia, a chlorine, bromine or iodine atom; the carbon atoms marked with an asterisk both having R or S configuration.

According to the description of said Italian patent applications, halogenating the compounds of formula I in which X=H leads to compounds of formula I in which X=halogen, in which there strongly prevails one of the two diastereoisomers with reference to the new centre of asymmetry which is generated (carbon atom to which the substituent X is bonded); rearranging the compounds of formula I in which X=halogen then leads to the corresponding optically active alpha-arylalkanoic acids.

If however compounds of formula I in which X=halogen are used for preparing optically active alpha-haloalkyl-aryl-ketones, ie compounds of formula

(in which Ar and R have the meanings given for formula I and X represents a chlorine, bromine or iodine atom), the ketal hydrolysis must be carried out under non-racemising conditions and in a reaction environment such that the product obtained (compound II) does not racemise. The normal ketal hydrolysis conditions (water and acid pH) have proved unsuitable because the hydrolysis requires drastic conditions and gives rise to the formation of undesirable by-products and racemisation of any ketone formed.

According to the present invention, we have now found that optically active compounds of formula II can be obtained by treating optically active ketals of formula I with a strong acid in a substantially anhydrous environment, possibly in the presence of an inert solvent.

In the compounds of formula II obtained in this manner, the enantiomeric excess reflects the diastereoisomeric excess of the starting compounds of formula I. The reaction is preferably conducted between 0° C. and 50° C., and in particular around 10°–15° C.

Suitable strong acids are methanesulphonic, sulphuric, p-toluenesulphonic, fluorosulphonic and trifluoromethanesulphonic acid, and generally those strong acids available in substantially anhydrous form.

To obtain acceptable reaction rates, an acid excess is used of around 3–10 times the compound of formula I by weight.

Depending on the nature of the substrate, it can be useful to use an organic solvent for optimising the results.

In all cases the organic solvent is used in small quantity, around 10–30% of the acid by weight.

Suitable solvents are lower alcohols, chlorinated hydrocarbons such as 1,2-dichloroethane and methylene chloride or their mixtures.

The following examples are described for the purpose of better illustrating the invention.

EXAMPLE 1

A mixture of diastereoisomers of 2-(1-bromoethyl)-2-(5-bromo-6-methoxy-2-naphthyl)-4(R),5(R)-dicarboxy-1,3-dioxolane (RRS:RRR=93:7; 5.04 g; 10 mmoles), methanesulphonic acid (20 ml) and methanol (5 ml) is kept at 20° C. for 18 hours. The reaction mixture is poured slowly into ice and extracted with dichloromethane.

The organic phase is washed with water and with a 2% sodium bicarbonate solution, and dried with sodium sulphate.

Evaporating the solvent under vacuum leaves a residue which on crystallisation from methanol provides pure 2-bromo-1-(5-bromo-6-methoxy-2-naphthyl)-propan-1-one (2.8 g; 7.5 mmoles; yield 75%).

M.P. 168°–170° C.

$[\alpha]_D^{20} = +153.4°$ (c=0.5, chloroform)

EXAMPLE 2

A mixture of diastereoisomers of 2-(1-bromoethyl)-2-(5-bromo-6-methoxy-2-naphthyl)-4(R),5(R)-dicarboxy-1,3-dioxolane (RRS:RRR=93:7; 2.52 g; 5 mmoles) and 96% sulphuric acid (15 ml) is kept at 20° C. for 20 minutes. The reaction mixture is processed as described in Example 1. In this manner, pure 2-bromo-1-(5-bromo-6-methoxy-2-naphthyl)-propan-1-one is obtained (0.8 g; 2.15 mmoles; yield 43%).

M.P. 166°–167° C.

$[\alpha]_D^{20} = +141.6°$ (c=0.5, chloroform)

$^1$H-NMR (200 MHz) analysis conducted as described in Example 1 shows a S(+):R(−) ratio of 94:6.

EXAMPLE 3

A mixture of diastereoisomers of 2-(1-bromoethyl)-2-(5-bromo-6-methoxy-2-naphthyl)-4(R),5(R)-dicarboxy-1,3-dioxolane (RRS:RRR=93:7, 4.03 g; 8 mmoles) and methanesulphonic acid (16 ml) is kept at 40° C. for 3.5 hours. The reaction mixture is then processed as described in Example 1.

In this manner, pure 2-bromo-1-(5-bromo-6-methoxy-2-naphthyl)-propan-1-one is obtained (2.6 g; 7 mmoles; yield 87.5%).

M.P. 166°–168° C.

$[\alpha]_D^{20} = +131.8°$ (c=0.5, chloroform)

$^1$H-NMR (200 MHz) analysis conducted as described in Example 1 shows a S(+):R(−) ratio of 91:9.

EXAMPLE 4

Conducting the reaction described in Example 3 at 20° C. for 18 hours, 2-bromo-1-(5-bromo-6-methoxy-2-naphthyl)-propan-1-one is obtained with a yield of 80%.

M.P. 167°–168° C.

$[\alpha]_D^{20} = +139.3°$ (c=0.5, chloroform)

$^1$H-NMR (200 MHz) analysis conducted as described in Example 1 shows a S(+):R(−) ratio of 93:7.

EXAMPLE 5

A mixture of diastereoisomers of 2-(1-bromoethyl)-2-(5-bromo-6-methoxy-2-naphthyl)-4(R),5(R)-dicarboxy-1,3-dioxolane (RRS:RRR=93:7, 4.03 g; 8 mmoles), methanol (4 ml) and methanesulphonic acid (16 ml) is kept at 20° C. for 18 hours. The reaction mixture is then processed as described in Example 1.

In this manner, pure 2-bromo-1-(5-bromo-6-methoxy-2-naphthyl)-propan-1-one is obtained (2.83 g; 7.6 mmoles; yield 95%).

M.P. 166°–168° C.

$[\alpha]_D^{20} = +140.32°$ (c=0.5, chloroform)

$^1$H-NMR (200 MHz) analysis conducted as described in Example 1 shows a S(+):R(−) ratio of 93:7.

EXAMPLE 6

Conducting the reaction described in Example 5 but starting with only the RRS diastereoisomer, optically pure 2(S)-bromo-1-(5-bromo-6-methoxy-2-naphthyl)-propan-1-one is obtained.

M.P. 166°–168° C.

$[\alpha]_D^{20} = +162.25°$ (c=0.5, chloroform)

$^1$H-NMR (200 MHz) analysis conducted as described in Example 1 shows the presence only of the S(+) enantiomer.

EXAMPLE 7

A mixture of diastereoisomers of 2-(1-bromoethyl)-2-(6-methoxy-2-naphthyl)-4(R),5(R)-dicarboxy-1,3-dioxolane (RRS:RRR=87:13; 12.5 g; 29.3 mmoles), methanol (15 ml) and methanesulphonic acid (60 ml) is kept at 20° C. for 1 hour. The reaction mixture is then processed as described in Example 1.

In this manner, optically pure 2(S)-bromo-(6-methoxy-2-naphthyl)-propan-1-one is obtained.

M.P. 90°–91° C.

I.R. (Nujol null) stretching C=O: 1680 cm$^{-1}$ $^1$H-NMR (90 MHz, CDCl$_3$-TMS) delta (ppm): 1.93 (d, 3H, J=7 Hz); 3.89 (s, 3H); 5.40 (q, 1H, J=7 Hz); 7.0–8.45 (aromatic protons, 6H).

$[\alpha]_D^{20} = +194.62°$ (c=0.5, chloroform)

$^1$H-NMR (200 MHz) analysis conducted as described in Example 1 shows the presence only of the S(+) enantiomer.

EXAMPLE 8

Conducting the reaction described in Example 7 but starting with the diastereoisomers of 2-(1-bromoethyl)-2-(6-methoxy-2-naphthyl)-4(R),5(R)-dimethoxycarbonyl-1,3-dioxolane (RRS:RRR=87:13), an entirely analogous result is obtained.

EXAMPLE 9

A mixture of diastereoisomers of 2-(1-bromoethyl)-2-(4-methylthiophenyl)-4(R),5(R)-dimethoxycarbonyl-1,3-dioxolane (RRS:RRR=92:8; 4.19 g; 10 mmoles), methanol (5 ml) and methanesulphonic acid (20 ml) is kept at 20° C. for 14 hours.

The reaction mixture is then processed as described in Example 1.

In this manner, pure 2-bromo-1-(4-methylmercaptophenyl)-propan-1-one is obtained (2.33 g; 9 mmoles; yield 90%).

I.R. (Nujol null) stretching C=O: 1680 cm$^{-1}$ $^1$H-NMR (90 MHz, CDCl$_3$-TMS) delta (ppm): 1.83 (d, 3H, J=6.6 Hz); 2.47 (s, 3H); 5.18 (q, 1H, J=6.6 Hz); 7.15–7.95 (AA'BB', 4H). 1H-NMR (200 MHz) analysis conducted as described in Example 1 shows a S(+):R(−) ratio of 89:11.

EXAMPLE 10

A mixture of diastereoisomers of 2-(1-bromoethyl)-2-phenyl-4(R),5(R)-dicarboxy-1,3-dioxolane (RRS:RRR=90:10; 1.035 g; 3 mmoles), methanesulphonic acid (0.53 ml; 6 mmoles) and dichloromethane (6 ml) is kept at 20° C. for 4 hours.

The reaction mixture is then processed as described in Example 1.

In this manner, 2-bromo-1-phenyl-propan-1-one is obtained in the form of an oil (0.4 g; 1.88 mmoles; yield 62%).

I.R. (neat) stretching C=O: 1680 cm$^{-1}$ $^1$H-NMR (90 MHz, CDCl$_3$-TMS) delta (ppm): 1.85 (d, 3H, J=6 Hz); 5.26 (q, 1H, J=6 Hz); 7.3–8.0 (aromatic protons, 5H).

1H-NMR (200 MHz) analysis conducted as described in Example 1 shows a S(+):R(−) ratio of 80:20.

We claim:

1. A process for preparing optically active alpha-haloalkyl-aryl-ketones of formula

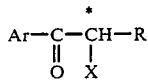

in which
- Ar represents an aryl, possibly substituted;
- R represents a $C_1$–$C_4$ alkyl; and
- X represents a chlorine, bromine or iodine atom, comprising reacting with a substantially anhydrous strong acid a compound of formula

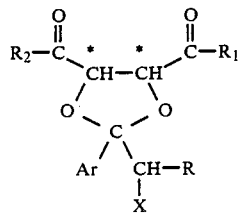

in which
- Ar, R and X have the meanings given for formula II;
- $R_1$ and $R_2$, which can be the same or different, represent a hydroxyl, an alkoxy, an amino group possibly mono- or di-substituted, or a $O^-M^+$ group where $M^+$ represents the cation of an alkaline metal; the carbon atoms marked with an asterisk both having R or S configuration; the carbon atom carrying the substituent X having mainly S or R configuration.

2. A process for preparing alpha-haloalkyl-arylketones as claimed in claim 1, characterised in that the compound I is reacted with strong acid at a temperature of between 0° C. and 50° C.

3. A process for preparing alpha-haloalkyl-arylketones as claimed in claim 1, characterized in that the compound I is reacted with strong acid at a temperature of 10°–15° C.

4. A process for preparing alpha-haloalkyl-arylketones as claimed in claim 1, characterised in that the compound I is reacted with strong acid in the presence of a solvent.

5. A process for preparing alpha-haloalkyl-arylketones as claimed in claim 1, characterised in that the compound I is reacted with strong acid in the presence of a solvent chosen from lower alcohols, chlorinated hydrocarbons and their mixtures.

* * * * *